United States Patent [19]
Crowder

[11] Patent Number: 5,133,776
[45] Date of Patent: Jul. 28, 1992

[54] PROSTHETIC VOLUME COMPENSATION DEVICE

[76] Inventor: Dan M. Crowder, 5302 Leawood, Pine Bluff, Ark. 71603

[21] Appl. No.: 805,540

[22] Filed: Dec. 11, 1991

[51] Int. Cl.⁵ .................................................. A61F 2/80
[52] U.S. Cl. ............................... 623/37; 128/DIG. 20
[58] Field of Search .................................... 623/33–37, 623/27; 128/DIG. 20

[56] References Cited

U.S. PATENT DOCUMENTS

| | | | |
|---|---|---|---|
| 2,634,424 | 4/1953 | O'Gorman | 623/37 |
| 3,309,714 | 3/1967 | Porten | 623/37 |
| 3,671,980 | 6/1972 | Baird | 623/37 |
| 3,889,301 | 6/1975 | Bonner, Sr. | 623/37 |
| 3,974,827 | 8/1976 | Bodeen | 128/DIG. 20 X |
| 4,432,101 | 2/1984 | Johnson | 623/37 |
| 4,655,779 | 4/1987 | Janowiak | 623/37 |
| 4,842,608 | 6/1989 | Marx et al. | 623/33 |
| 4,923,475 | 5/1990 | Gosthnian et al. | 623/37 |

Primary Examiner—Ronald Frinks
Attorney, Agent, or Firm—Ray F. Cox, Jr.

[57] ABSTRACT

The present invention provides for an air cell or cells which may be placed into an existing prosthesis or incorporated into a newly fabricated prosthesis. The air cell is provided with means for manually adjusting the degree of inflation of the air cell so that changes in volume of the residual limb may be compensated for as required. Inflation of the air cell is accomplished by a fingertip operated pump which incorporates a valve for exhausting air from the air cell. The air cell is provided with a number of internal beams which limit the inflation of the air cell to prevent ballooning. One embodiment of the invention incorporates an internal needle valve to allow removal of the air pump.

5 Claims, 2 Drawing Sheets

PROSTHETIC VOLUME COMPENSATION DEVICE

BACKGROUND OF THE INVENTION

The present invention relates to prostheses and more particularly to volume compensation devices for adjusting the fit of a prosthetic socket to a residual limb.

Those individuals who have suffered an amputated limb are generally fitted with prosthetic devices which are provided with a socket into which the residual limb is inserted. Maximum usefulness of artificial limbs is enhanced by maintaining a close and comfortably fitting prosthetic socket.

One critical problem in assuring such a close and comfortable fit for a prosthetic socket is that the fit of the prosthetic socket is affected by daily variations in the volume of the residual limb. For example, merely walking on a residual limb may cause the volume of the limb to be reduced to the point that a comfortably fitting socket becomes unacceptably loose fitting.

In the past various inflatable or volume adjustable devices have been proposed for use in conjunction with prosthetic sockets. These devices, however, have primarily been directed toward the functions of cushioning the end of the residual limb or of a clamping action to assure the securing of a prosthetic appliance to a residual limb.

For example, U.S. Pat. No. 4,842,608 issued to Marx et al. on Jul. 27, 1989 for "Fluctuating Volume Adjustable Preparatory Below Knee Prosthetic Socket", a pair of cooperating rigid plastic supports relatively adjustable to accommodate volume changes in residual limbs. However, Marx is primarily directed to the problem of post-operative changes in residual limb volume and not to daily variations.

Numerous air or fluid inflatable prosthetic devices have been developed essentially to act as a substitute for a custom fitted prosthetic socket. These devices are designed to cushion the residual limb and to provide a tight fit for securing the residual limb to the prosthetic device. For example, U.S. Pat. No. 2,634,424 issued to O'Gorman on Apr. 14, 1953 for "Artificial Leg" discloses a prosthetic socket made of a resiliently flexible material whose walls are spaced apart to provide an air-tight cavity with a series of webs dividing it into a number of interconnected departments. The device completely encircles the residual limb and is provided with mean to inflate or deflate the device. The device, however, is not designed to readily accommodate short term daily fluctuations in the volume of the residual limb. Likewise, U.S. Pat. No. 3,393,407 issued to Kandel on Jul. 23, 1968 for "Artificial Limb with End-Bearing Socket and Method of Making" is also primarily a substitute for a custom fitted socket. No means to adjust the volume of the socket is provided. U.S. Pat. No. 3,889,30 issued to Bonner on Jun. 17, 1975 for "Therapeutic Stump Treating Air Sac Prosthesis" falls in the same category. U.S. Pat. No. 4,655,779 issued to Janowiak on Apr. 7, 1987 for "Air System Prosthesis for Amputees" provides for a manual means to inflate and deflate an air sac which completely surrounds the residual limb. While Janowiak provides means for adjusting the volume of the prosthetic socket, Janowiak, likewise, is directed to a device which substitutes for a custom-made socket and includes features primarily designed to cushion the residual limb and to assist in securing the prosthesis to the residual limb.

In the same category of inflatable devices whose primary purpose is to provide cushioning for the end of the residual limb is U.S. Pat. No. 4,923,475 issued to Gosthnian, et al. on May 8, 1990 for "Inflatable Limb Prosthesis with Preformed Inner Surface." Gosthnian discloses a prosthesis having a socket with a plurality of inflatable bladders. The inflatable bladders are located in such a way as to cushion the weight bearing portions of the residual limb. A variant cushioning device is disclosed in U.S. Pat. No. 4,432,101 issued to Johnson on Feb. 21, 1984 for a "Cushioning Patellar Support Device." Johnson discloses a butterfly shaped inflatable/deflatable bag for cushioning the weight bearing portions of the residual limb in conjunction with a below-the-knee prosthesis.

An example of an inflatable device designed primarily to secure the residual limb to the prosthesis is disclosed in U.S. Pat. No. 3, 671,980 issued to Baird on Jun. 27, 1972 for "Fluid Pressure Clamp for Prosthetic Appliance." Baird discloses a fluid pressure wedge for securing a prosthetic appliance to the residual limb.

None of the cited devices, however, is uniquely adapted to the problem of daily fluctuations in the volume of a residual limb when used in conjunction with a normal, custom-fitted prosthetic socket.

SUMMARY OF THE INVENTION

It is the purpose of the present invention to provide a device which may be retro-fitted into existing prostheses a well as incorporated into newly fabricated prostheses to overcome the problem of daily fluctuations in the volume of residual limbs. To attain this objective, the present invention provides for an air cell or cells which may be placed into an existing prosthesis or incorporated into a newly fabricated prosthesis. The air cell is provided with means for manually adjusting the degree of inflation of the air cell so that changes in volume of the residual limb may be compensated for as required. Inflation of the air cell is accomplished by a fingertip operated mini-pump which incorporates a valve for exhausting air from the air cell if necessary. The air cell and accompanying mini-pump may be mounted in a variety of ways, depending upon both comfort and aesthetic considerations. The air cell, itself, is provided with a number of internal beams which limit the inflation of the air cell to prevent ballooning. In one embodiment of the present invention the air cell is provided with a normally closed needle valve so that in certain applications the air pump may be removed and pressure maintained within the air cell. This embodiment allows for the pump to be removed if aesthetic or design considerations would prohibit its remaining attached to the air cell.

It is, therefore, an object of this invention to provide a means for adjusting the volume of a prosthetic socket to respond to changes in the volumes of residual limbs.

It is a further object of the present invention to provide for a device that may be conveniently and easily operated by the user of the prosthesis.

It is also an object of the present invention to provide for retro-fitting into existing prostheses as well as allowing incorporation of the device into newly fabricated prostheses.

It is still a further object of the present invention to provide for a device whose installation is comfortable and aesthetically pleasing.

These and other objects and advantages of the present invention will become apparent from a reading of the following detailed description of the invention in conjunction with the following drawings.

DETAILED DESCRIPTION OF THE INVENTION

Figure 1:
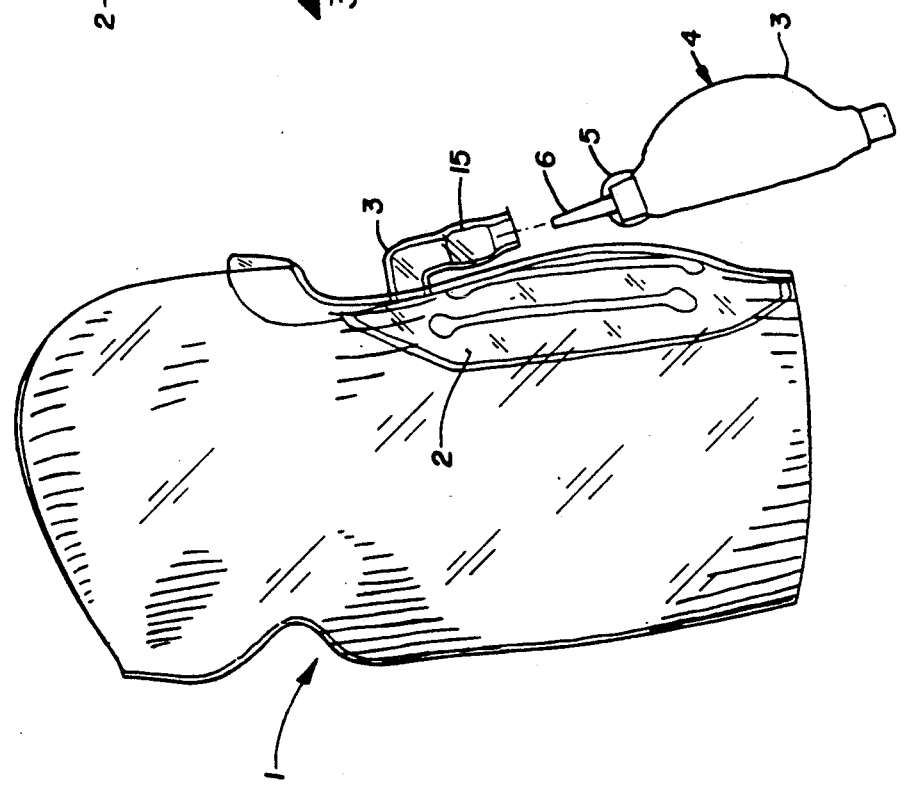
FIG. 1 is a side elevation of a typical prosthetic socket showing the invention in place against the rear wall of the socket. The particular embodiment of the invention in this drawing is that of an angled coupling which allows a hand operated air pump to lie close to the rear wall of the prosthetic socket. The air pump is shown in an exploded view in relation to the angled coupling.

With reference to FIG. 1, a standard prosthetic socket is designated generally as 1. One particular placement of the air cell 2 is shown. In use, the air cell 2 may be placed in an area of the socket 1 which most closely matches the largest flat surface of the socket 1 adjacent to a soft tissue area. In FIG. 1 the air cell 2 is located in the posterior wall of the socket 1. The air cell 2 communicates with an angled coupling 3. As will be described below, a straight coupling may also be employed in an alternative embodiment.

The angled coupling 3 is adapted to receive a miniature hand pump 4 of a type well known in the art. The hand pump 4 comprises a flexible hand manipulable bellows section 3, a hand manipulable valve 5 which ma be used to controllably release air from the air cell 2, and a nipple 6 which is insertable and removable from the angled coupling 3. The angled coupling 3 is provided with means for lockably engaging the nipple 6 of the hand pump 4 in an air-tight manner. For example, an annular ring 15 of soft rubber is employed in the preferred embodiment In an alternative embodiment, the hand pump 4 may be connected to the angled coupling 3 through an air line which would allow the hand pump 4 to be physically located at a distance from the angled coupling 3.

In use the hand pump 4 is connected to the angled coupling 3. The hand pump 4 communicates through the angled coupling 3 to the interior of the air cell 2. Manipulation of the hand pump 4 allows the air cell 2 to be inflated to the desired degree of comfort. The user may also operate the valve 5 to reduce air pressure in the air cell 2 if necessary to accommodate increases in volume of the residual limb. The embodiment of the invention shown in FIG. 1 incorporates an angled coupling 3. The angled coupling 3 allows the hand pump 4 to be inserted into the angled coupling 3 such that the air pump 4 lies along the exterior posterior wall of the socket 1. In this configuration the portions of the invention external to the socket 1 are relatively innocuous and may easily be camouflaged for a more aesthetic appearance to the artificial limb.

Figure 2:
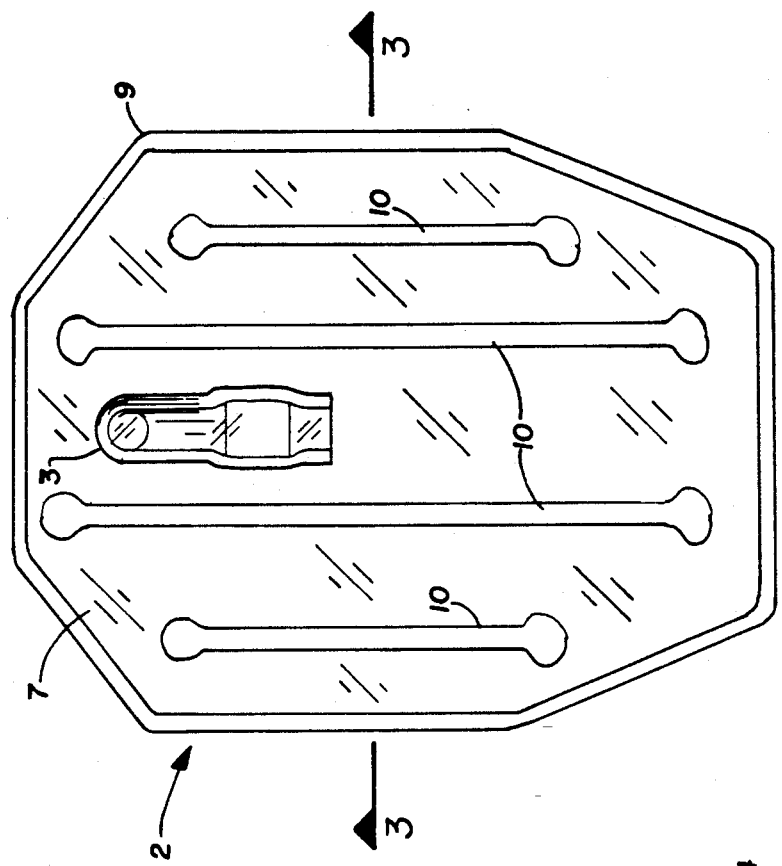
FIG. 2 is a plan view of one embodiment of the invention showing an angled coupling and the location of the internal beams.

The air cell 2 may be designed in a number of various shapes and sizes to conform to the appropriate soft tissue areas of the residual limb. FIG. 2 shows a plan view of a typical configuration which will be used to illustrate the construction of the air cell 2. The air cell 2 is constructed of two layers of pliable air tight material The upper layer 7 is visible in FIG. 2. Suitable materials for the two layers would include 10 mil polyurethane backed with 420 denier nylon. Other pliable air tight materials would also be suitable The two layers 7 and 8 are radio frequency welded along their edges to form an air tight bladder. The air tight sealed edge is designated 9.

Figure 3:
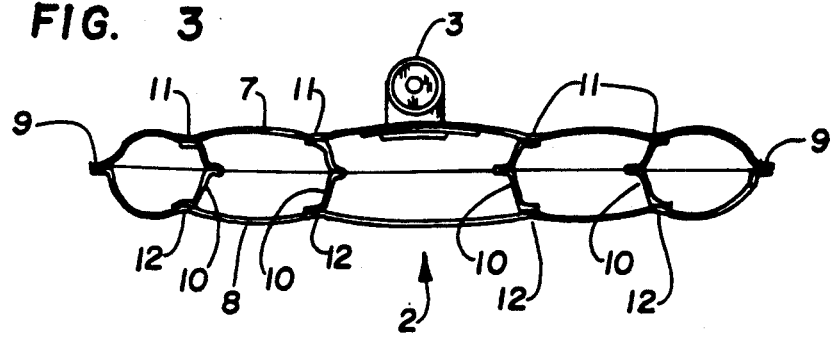
FIG. 3 is a sectional view of the device shown in FIG. 2 when inflated.

Referring to FIG. 3, in order to prevent "ballooning" of the inflated air cell 2, a system of internal beams 10 is provided to limit thickness of the inflated air cell 2 to a predetermined amount. The internal beams 10 are comprised of lengths of substantially rectangular pliable material First edges 11 of the internal beams are radio frequency welded to the upper layer 7 and second edges 12 of the internal beams 10 are radio frequency welded to the lower layer 8. Referring to FIG. 2, the bonded edges of the internal beams 10 are arranged so that inflation air is able to flow to all parts of the air cell 2 without constriction. The arrangement by which the internal beams 10 are welded to the upper layer 7 is shown in FIG. 2.

With reference again to FIG. 3, the angled coupling 3 is attached to the upper layer 7 such that the angled coupling 3 communicates with the interior of the air cell 2.

Figure 4:
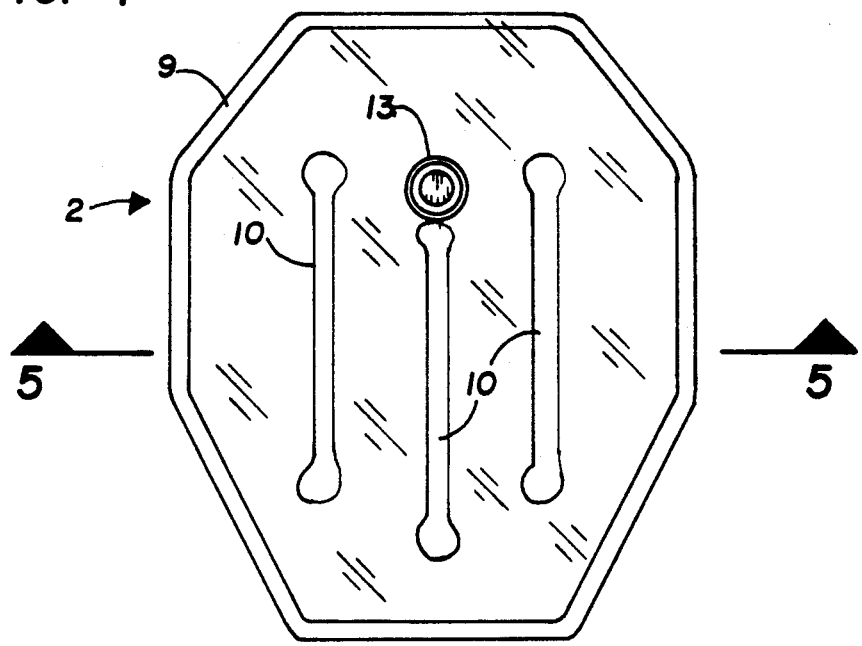
FIG. 4 is a plan view of an alternative embodiment of the invention showing a reduced number of internal beams and a straight rather than an angled coupling.
Figure 5:
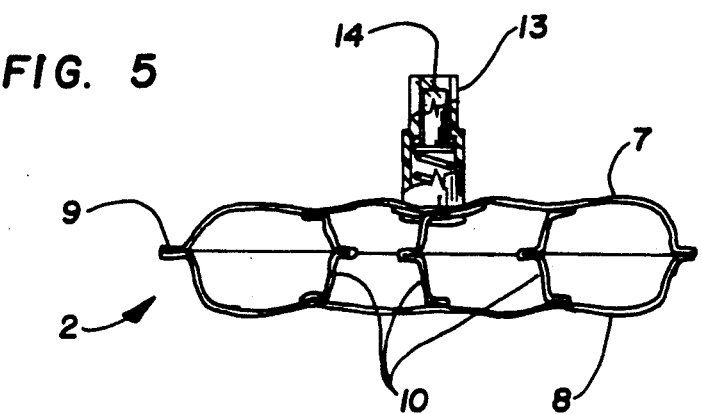
FIG. 5 is a sectional view of the embodiment of the invention shown in FIG. 4 when inflated showing the use of the normally closed internal needle valve in conjunction with the straight coupling

With reference to FIG. 4, a different arrangement of the internal beams 10 for a smaller air cell is illustrated. Furthermore, FIG. 4 shows an alternative straight coupling 13 which is illustrated in cross section on FIG. 5. The embodiment of the straight coupling 13 shown in FIG. 5 incorporates an internal needle valve 14. The angled coupling 3 may also embody an internal needle valve 14. The internal needle valve 14 is normally closed when the air cell 2 is inflated. Insertion of the nipple 6 of the hand pump 4 acts to open the needle valve 14. Thus, while the hand pump 4 is inserted in the straight coupling 13 the manner in which the invention is operated and used is identical to that used when no needle valve 14 is employed. However, the straight coupling 13 or the angled coupling 3 incorporating the needle valve 14 has the additional advantage that removal of the hand pump 4 allows the needle valve 14 to close and maintain air pressure within the air cell 2 even though the hand pump 4 has been removed. This variation on the preferred embodiment is appropriate when aesthetics or practical considerations preclude allowing the hand pump 4 to remain attached while the invention is in use.

Although the embodiments described above have focused on the use of a single air cell 2 in a prosthetic socket, certain applications may require the use of multiple air cells. In such a case, multiple hand pumps 4 could be employed, or alternatively, a single hand pump 4 connected to the multiple air cells 2 through a T-coupling or similar means.

It is, therefore, apparent that the present invention offers the advantages described above. The present invention offers a high degree of flexibility in its use with either existing prostheses or newly fabricated prostheses. The invention has the advantage of flexibility in use through placement in a variety of positions within the prosthetic socket. Furthermore, the present invention may be used both with and without a hand pump attached allowing great flexibility in accommodating aesthetic and practical requirements in the use of the device.

Although the present invention has been described with reference to a preferred embodiment and certain alternatives thereto, it will be understood that other variations may be made to the present invention without departing from the spirit and scope of the invention as set forth in the following claims.

What is claimed is:

1. A pneumatic, volume-compensating device for use in conjunction with a prosthesis having a socket defined by stiff peripheral walls for receiving a residual limb, said device comprising:

first and second layers of pliable air-tight material shaped to conform to the appropriate soft tissue areas of the residual limb, said layers having edges bonded together to form a substantially planar, air-tight bladder insertable in said socket, said layers further having inner and outer surfaces;

a plurality of internal beams, comprising lengths of substantially rectangular pliable material, each of said internal beams having a first and a second longitudinal edge and a transverse dimension selected to limit the thickness of said air-tight bladder to a predetermined amount, when inflated, by having said first longitudinal edges bonded to said inner surface of said first layer and said second longitudinal edges bonded to said inner surface of said second layer;

air inlet means communicating with said air-tight bladder for supplying thereto and exhausting therefrom pressurized air; and a manually operable air pump communicating with said air inlet means for supplying pressurized air to said air inlet means, said air pump further having a manually operable valve for exhausting pressurized air therefrom 2. A device as set forth in claim 1, wherein said air inlet means comprises a straight coupling affixed substantially perpendicular to said air-tight bladder, said straight coupling further having sufficient length to extend through said peripheral walls of said socket 3. A device as set forth in claim 2, wherein said air inlet means further comprises a needle valve in conjunction with said straight coupling such that the insertion of said manually operable air pump into said straight coupling opens said needle valve while the removal of said manually operable air pump allows said needle valve to close and retain air pressure within said air-tight bladder.

4. A device as set forth in claim 1, wherein said air inlet means comprises an angled coupling having a first portion affixed substantially perpendicular to said air-tight bladder and communicating with a second portion at right angle to said first portion such that said first portion has sufficient length to extend through said peripheral walls of said socket and said second portion lies outside of and substantially parallel to said peripheral walls of said socket.

5. A device as set forth in claim 4, wherein said air inlet means further comprises a needle valve in conjunction with said angled coupling such that insertion of said manually operable air pump into said angled coupling open said needle valve while the removal of said manually operable air pump allows said needle valve to close and retain air pressure within said air-tight bladder.

* * * * *